United States Patent [19]

Neumer

[11] Patent Number: 5,254,744
[45] Date of Patent: Oct. 19, 1993

[54] PREPARATION AND PURIFICATION OF POLY(TETRAMETHYLENE ETHER) FORMAL GLYCOLS AND POLY(OXYBUTYLENE FORMAL) GLYCOLS

[75] Inventor: John F. Neumer, Hockessin, Del.

[73] Assignee: E. I. Du Pont de Nemours and Company, Wilmington, Del.

[21] Appl. No.: 843,884

[22] Filed: Feb. 28, 1992

[51] Int. Cl.[5] .............................. C07C 43/303
[52] U.S. Cl. .................... 568/601; 568/603; 568/594; 568/121
[58] Field of Search ............... 568/601, 603, 594, 621

[56] References Cited

U.S. PATENT DOCUMENTS

| | | | |
|---|---|---|---|
| 2,535,458 | 12/1951 | Robeson | 568/594 |
| 2,786,081 | 3/1957 | Kress | 568/601 |
| 2,979,533 | 4/1961 | Bruson et al. | 568/601 |
| 3,959,277 | 5/1976 | Chang et al. | 260/67 TN |
| 4,340,719 | 7/1982 | Pechhold | 528/230 |
| 4,355,119 | 10/1982 | Pechhold | 521/159 |
| 4,665,220 | 5/1987 | Gregory et al. | 568/697 |

OTHER PUBLICATIONS

Hill and Carothers, "Cyclic and Polymeric Formals", Journal of the American Society, vol. 57, pp. 925-928 (1935).

Schonfield, "Preparation and Physical Properties of a Homologous Series of Polyformal Urethanes", Journal of Polymer Science, vol. 59, pp. 87-92 (1962).

Vogel, Textbook of Practical Organic Chemistry, Logmanas et al, New York, 1951 pp. 144-145.

*Primary Examiner*—Howard T. Mars

[57] ABSTRACT

Oligomeric formal diols are prepared by coupling segments of poly(tetramethylene ether) glycols, each having a molecular weight of 650-3000, with formaldehyde in the presence of a granular acidic catalyst, to yield poly(tetramethylene ether) formal glycols of 1,400-12,000 molecular weight.

Oligomeric formal diols of a second type can also be prepared by coupling with formaldehyde segments of poly(tetramethylene ether) glycols mixed with segments of other polymeric glycols, as for example polyethylene oxide glycol of 200 molecular weight, to yield poly(ether formal) glycols of substantially higher molecular weight than either of the starting polyether glycols, and having properties significantly different from the parent polyether glycols that may affect the performance as soft or elastomeric segments of derived polyurethanes, polyetheresters, and polyureas.

Yet a third type of oligomeric formal diols can be prepared by coupling monomeric diols, as for example 1,4-butanediol, with formaldehyde to yield higher molecular weight poly(oxybutylene formal) glycols.

13 Claims, No Drawings

PREPARATION AND PURIFICATION OF POLY(TETRAMETHYLENE ETHER) FORMAL GLYCOLS AND POLY(OXYBUTYLENE FORMAL) GLYCOLS

BACKGROUND OF THE INVENTION

1. Field of the Invention

This invention relates to the field of preparing poly(ether formal) glycols, and more specifically relates to synthesis of block poly(tetramethylene ether formal) glycols, block hybrid poly(ether formal) glycols, and oligomeric formal glycols from paraformaldehyde and, respectively, poly(tetramethylene ether) glycols, mixtures of poly(tetramethylene ether) glycols with polyethylene oxide glycols and/or polypropylene oxide glycols including substituted polyethylene oxide glycols, or alpha-omega diols such as monomeric 1,4-butanediol.

2. Description of the Related Art

Poly(tetramethylene ether) glycols, herein abbreviated as PTMEG, are commercially available and widely used as polyols along with a polyisocyanate and a chain extender in high performance polyurethanes. They are also used in polyetheresters and polyureas. PTMEG acts as an elastomeric soft segment in these products, while the chain extender and polyisocyanate or polyester contribute crystalline hard blocks to the final polymer structure. Several molecular weight ranges of PTMEG are made to cover a variety of end uses: Mn 650, 1000, 2000, and 2900 are typical. Molecular weights above 2000 cause the PTMEG to be difficult to handle because of its high viscosity. Further, even at 650 molecular weight, PTMEG is a borderline solid while higher molecular weights must be melted before use in most applications.

One approach to provide a lower melting modified PTMEG is to couple segments of the PTMEG with formaldehyde to break up the regular polyether structure as illustrated:

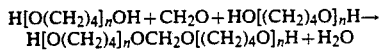

Also, 3 moles of PTMEG + 2 moles of formaldehyde should yield

These block PTMEG formal glycols, block hybrid poly(ether formal) glycols, and oligomeric formal glycols are characterized by lower crystalline melting points and lower viscosities than the corresponding PTMEG of similar molecular weight indicating a more random arrangement of the backbone structure of the glycols, and thus making these products easier to handle in their manufacture, shipping, storage, and processing in further reactions. Also included is a polymer of the formula:

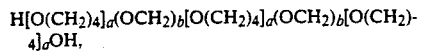

where the "a" components are derived from poly(tetramethylene ether) glycols of 650–3,000 Mn and "b" components are derived from formaldehyde or paraformaldehyde and may represent 0–3 or more (OCH$_2$) formaldehyde linkages.

The invention relates to modification of poly(tetramethylene ether) glycols (PTMEG) to improve low temperature flexibility, alter hydrophilic/hydrophobic character, and affect water vapor transmission of the final polymers including polyurethanes, polyureas and polyetheresters made by incorporating the modified PTMEG. In addition, the modified poly(tetramethylene ether) glycols have lower melting points and lower viscosity than PTMEG of corresponding molecular weight, thus making easier handling of the materials in their manufacture, shipping, storage, and further reactions.

Some potential uses for the new oligomeric formal diols require further purification, for example to reduce trace impurities interfering with accurate molecular weight determination of the product, and to reduce the color of the oligomeric formal diols and their derived end-use polymers. A purification procedure in which the crude formals are treated with an aqueous calcium hydroxide solution, under conditions of steam distillation purging to destroy color-forming formaldehyde residues is an integral part of the preparation of the high quality formal glycols of this invention.

3. Description of the Prior Art

"Oligomeric Formal Diols of Poly(tetramethylene ether) Glycols and Polyurethanes Therefrom" is the subject of Pechhold U.S. Pat. Nos. 4,340,719 and 4,355,119. Pechhold prepared formal diols by coupling up to four PTMEG segments, each having a molecular weight of 1000–3000 with formaldehyde in the presence of a strongly acidic cationic ion exchange resin bearing —SO$_3$H groups, insoluble in the PTMEG, as catalyst. Rohm & Haas "Amberlyst" XN-1010 was satisfactory. The reaction medium was an aromatic hydrocarbon (toluene) at reflux temperature (110° C.). Any water liberated by the coupling reaction was distilled off. The reaction vessel was then cooled, the contents were filtered to remove the catalyst, and toluene was stripped using a rotary evaporator to leave the oligomeric formal glycol.

For some applications, the oligomeric poly(tetramethylene ether formal) glycols so prepared require further treatments to satisfy commercial end use requirements.

British Patent 850,178 (Hudson Foam Plastics Corporation), Sep. 28, 1960, claims "A process for producing polymeric formals having a molecular weight of at least 1270, a hydroxyl number of less than 200 and terminal hydroxyl groups, comprising reacting a hydroxyl compound [one or more hydroxyl-terminated glycols] with formaldehyde in the presence of an acidic catalyst and separating the evolved water by the application of vacuum to the reaction mixture, the process being carried out at temperatures not exceeding 130° C. and the reaction being continued until the desired degree of polymerization has been attained."

Page 1, line 63 states: "Thus, for example, under preferred conditions of the present invention, tetramethylene glycol gives rise to a reaction product including from 70 to 80% polymer and from 20 to 30% of a cyclic monomer having a boiling point of 116°–117° C. at 775 mm. of mercury. Glycols with more than four atoms between the hydroxyl groups result in reaction products having even larger proportions of polymer and correspondingly less monomer."

Published Japanese Patent Application 18598/75 to Nippon Soda Company broadly discloses reacting a polyetherpolyol with formaldehyde in the presence of sulfuric or phosphoric acid catalysts, and suggest that Friedel-Crafts catalysts can generally be used. The products were evaluated for preparation of both soft and hard polyurethane foams.

Chang et al., U.S. Pat. No. 3,959,277, May 25, 1976, point out that polyformals from alpha, omega-diols having at least 4 carbon atoms in a single chain are greatly improved for use in polyurethanes if the polyformal has a low methylol end-group content by treatment with alkali metal sulfite or bisulfite. The alpha, omega glycols of the examples are 1,6-hexanediol and thiodiethanol. 1,4-Butanediol and diethyleneglycol are listed as suitable co-monomers. In the best examples the methylol end group concentration was of the order of 2%. The methylol end-group content of the present poly(alkylene ether formal) glycols is believed to be essentially zero.

Cyclic and polymeric formals from alpha, omega-diols and formaldehyde were also investigated by Hill and Carothers, Journal of the American Chemical Society, Vol. 57, pages 925-928 (1935), and by Schonfeld, Journal of Polymer Science, Vol. 59, pages 87-92, (1962). Ethylene glycol, trimethylene glycol, and 1,4-butanediol yield the 5 member ethylene formal, the 6 member 1,3-dioxane (trimethylene glycol, and 1,4-butanediol yield the 5 member ethylene formal, the 6 member 1,3-dioxane (trimethylene formal), and the 7 member tetramethylene formal; all of these were isolated. Other monomeric formals made include the 8 member pentamethylene formal. The 9 member hexamethylene formal, the 12 member nonamethylene formal, the 13 member decamethylene formal, the 17 member tetradecamethylene formal, and the 21 member octadecamethylene formal. Attempts were made to polymerize these cyclic monomers at 150° C. in the presence of a trace of sulfonic acid. The 6 member ring trimethylene formal could not be induced to polymerize. However, the monomer tetramethylene, pentamethylene, and triethylene glycol formals quickly became more viscous under the polymerization conditions.

The polyformal glycol from 1,4-butanediol and paraformaldehyde of this invention contains a portion of the formal —O(CH$_2$O)— units present in a block oligomeric structure —O(CH$_2$O)$_n$—. In the practice of this invention, the number of formal units engaged in blocks is 0.5 to 30% of all formal units present. While the latter percentage is known precisely from NMR (nuclear magnetic resonance) observation, the value of n in the blocks is indeterminate, as is also the number of blocks with n greater than 1.

The above new composition of matter sets the compounds of this invention apart from those claimed in the previous art of making poly(oxybutylene formal) glycols in which the polymeric species have been described as the regular polymer of what could be considered the monomeric 1,4-butanediol formal.

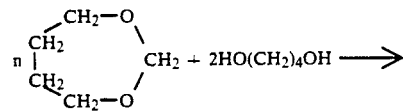

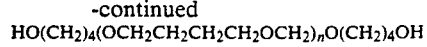

Further, the polymeric material of this invention posses no terminal hemiacetal links as determined by the invariance of the NMR carbon 13 spectrum to reaction of the polymer with aqueous sodium bisulfite solution, a treatment known to show hemiacetal end groups if present as described by Chang et al., U.S. Pat. No. 3,959,277 above.

The presence of the polyformal block units in the above soft segment preparation is unexpected on the basis of the earlier art and, as a feature of which introduces chain disorder into the soft segment backbone, is a valued formal physical property which imparts liquidity to formals of higher molecular weight. The same disorder can impart improved low temperature performance to polyurethanes prepared from other poly(oxyalkylene formal) glycols.

DETAILED DESCRIPTION OF THE INVENTION

The process of this invention solves two major problems in the prior art process of U.S. Pat. Nos. 4,340,719 and 4,355,119:

1) Preparation of PTMEG formals with minimum loss of PTMEG segment molecular weight through depolymerization to tetrahydrofuran (THF), thus favoring greater control over product molecular weight.

2) Preparation of poly(ether formal) glycols that do not strongly develop color when treated with inorganic or organic bases at elevated temperatures, and therefore do not cause interference with the commonly used hydroxyl number determination for number average molecular weight, ($M_n$), of the product. This may also be important in preparation of many elastomeric polyurethanes, polyetheresters, and polyureas incorporating these soft segments.

Additional advantages of this invention are:

3) A practical route to entirely new classes of poly(ether formal) glycol soft segments that can be prepared with physical properties superior to currently offered products.

4) A simple process capable of modifying the physical properties of polyether glycol soft segments for specific end use functions by generating a variety of new hybrid poly(ether formal) glycols.

Generally, the present invention involves a process comprising mixing paraformaldehyde (or any other form of formaldehyde) with one or more diols in a cyclohexane solvent, in the presence of an acidic, granular montmorillonite catalyst. Preferably, the reaction product is purified by steam distillation in the presence of calcium hydroxide to yield a product having a very low color of less than 5 APHA units.

The diols used may be any of three categories as follows:

(a) poly(tetramethylene ether) glycol having a molecular weight of 650 to 3,000, (b) poly(tetramethylene ether) glycol having a molecular weight of 650 to 3,000 and one or more glycols of the formula HO($C_xH_{2x}$O)$_n$H where x is 2 or 3 and n is from 5 to 50, and (c) a diol of the formula HOC$_y$H$_{2y}$OH where y is 2 to 4.

In (b) —$C_xH_{2x}$— preferably is

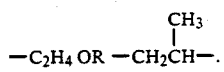

In (c) —$C_yH_{2y}$— preferably is

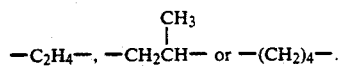

Generally, the reaction should be carried out in an inert atmosphere. A nitrogen blanket is suitable for providing an inert atmosphere. The use of a steam heated reaction vessel jacket provides a method for rapidly bringing the reaction to the desired reaction temperature. Generally, the preferred reaction temperature is from 80° to 81° C. The reaction medium normally is held at the reaction temperature until the predetermined volume of water distillate is collected, generally 2 to 4 hours. The catalyst generally will be present in an amount of from 1 to 10 weight percent and preferably about 4 to 6 weight percent, as based on initial charge of formaldehyde and diol, i.e. (a), (b) or (c), to the reaction medium.

The process of the present invention enables the production of a wide variety of formals including those derived from polyether glycols involving poly(tetramethylene ether) glycol, mixtures thereof with poly(ethylene ether) glycol or poly(propylene ether) glycol. Further hybrid formal copolymers of formaldehyde with any combination of 1,4-butane diol, ethylene glycol or propylene glycol or other polyols can be prepared in accordance with the process of the present invention.

Generally, the molar ratio of formaldehyde to moles of diol (a), (b) or (c) can be varied to attain the preselected number average molecular weight of the formal coupled product in accordance with the principle that if n moles of glycol are to be coupled then (n−1) theory equivalents of formaldehyde are required. In practice the range of molar quantities of formaldehyde (typically added as paraformaldehyde) used can be 0.9(n−1) to 1.10(n−1). The above diolformaldehyde mixtures, together with 1.0 to 10.0 weight percent of solid, granular montmorillonite catalyst (based on the weight of the diol) in cyclohexane is heated at the reflux temperature for a period sufficient to remove the water of reaction by azeotropic distillation (2–4 hours). By this procedure formal coupled diol products are recovered which, in the case of (a) and (b) have number average molecular weights of 1300 to 10,000, and in the case of (c) have number average molecular weights of 800–3000.

Preferably, the reaction product of formaldehyde and (a), (b) or (c) is steam distilled in the presence of calcium hydroxide to provide a product having an APHA color of less than 10 and preferably less than 5. This involves mixing from 1% to 5% of calcium oxide (by weight of crude formal) preferably 3.75%, or 1.32% to 6.60% of calcium hydroxide, preferably 5.0%, with the reaction product of formaldehyde and (a), (b) or (c) and then blowing steam through the mixture for 2 to 4 hours. Generally, the temperature used for steam distillation is from 99° to 100° C. at atmospheric pressure.

The process of the present invention enables the production of oligomeric glycols in which the polyether connecting backbone are comprised of formals of

- like units of polyether glycols of the same number average molecular weight, e.g., PTMEG 1000.
- like units of polyether glycols of different number average molecular weight, e.g., PTMEG 1000 and 650, in any and all combinations of molar ratios.
- mixtures of different polyether glycols, each of the same or different number average molecular weights, e.g., PTMEG 1000 with PEG 200, in any and all combinations of molar ratio.
- glycols with carbon backbones in any configuration with molecular carbon content of $C_2$ to $C_6$, e.g. 1,4-butene diol.
- mixtures of glycols with carbon backbones in any configuration with molecular carbon content of $C_2$ to $C_6$, wherein the molar ratios of the individual glycols can be in any and all combinations.
- hybrid formals of mixtures of any of the above polyether glycol formals.

The following advantages of the poly formal glycols as characterized above can be listed:

1. The subject products can be liquid at room temperature as desired for ease of prepolymer formation.
2. Controlled modulation of water permeation in the formal derived polyurethane, polyester and polyurethane elastomers.
3. Controlled modulation of oil resistance in the formal derived elastomers.
4. Preparation of some transparent elastomers which otherwise would have been opaque.
5. Preparation of derived elastomers with superior low temperature flexibility.
6. Facile formulation of hetero-aggregate mixtures of prepolymers with filling ingredients as in the fabrication of solid rocket fuels.

Advantages over the prior art:

1. Lower temperature of operation during synthesis limits depolymeration of the backbone PTMEG and increases product yield.
2. Superior molecular weight control of the formal product by monitored removal of predetermined amounts of the byproduct water.
3. The new formation of hybrid block formals of polyether glycols allows for tailoring of specific properties of the glycol soft segment used in polyurethane and other polymeric elastomer formulations such as lower viscosity and lower melting points. These properties of the soft segment glycol directly influence advantageous properties in the prepolymer and in the final polyurethane elastomeric product.
4. The direct formation of poly(oxybutylene formal) diols without prior formation and isolation of the monomeric cyclic formal and its subsequent, independent polymerization.
5. A purification scheme for crude poly(ether formal) glycols and poly(oxybutylene formal) glycols which frees the desired formal diols from by-products inherent in the acid catalyzed formal synthesis. This by-product formation is made manifest by a yellow foreign body which forms when the crude formal (colorless) is treated with an inorganic base at 98° to 100° C. under the conditions of steam distillation. The yellow by-product formed under these conditions is water soluble and thus easily separated from the purified formal organic phase. A clear benefit of this purification is in improved facility in hydroxyl number determination of the formal product.

EXAMPLE 1

Preparation of Teratbane ® 650×3 Formal

TERATHANE ® POLYETHER GLYCOL 650 is a commercial product available from the Du Pont Company. It is poly(tetramethylene ether) glycol with a number average molecular weight ($M_n$) of 650 as determined by hydroxyl number titration with acetic anhydride according to ASTM-D-1638 and converting this number to number average molecular weight according to the formula:

$$\text{Number of average molecular weight} = \frac{56,000 \times m}{\text{hydroxyl number}}$$

where m is the hydroxyl functionality of the sample.

The reaction chemistry is:

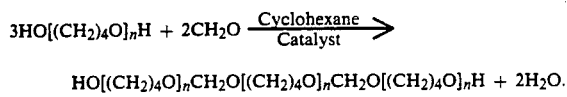

$HO[(CH_2)_4O]_nCH_2O[(CH_2)_4O]_nCH_2O[(CH_2)_4O]_nH + 2H_2O$.

The reaction was carried out in a steam jacketed, 4 necked, 5 liter flask equipped with an air-powered propeller stirrer, an efficient condenser, a Dean-Stark trap, and a nitrogen blanket.

The reaction vessel was charged with,
1950 g TERATHANE ® polyether glycol 650,
90.1 g paraformaldehyde,
108.0 g Catalyst KO, an acidic montmorillonite clay, granular catalyst available from Sud Chemie,
1500 ml cyclohexane.

The reaction vessel was purged with nitrogen and vigorously stirred. Steam was passed through the jacket to give a rapid reflux of the cyclohexane while water entrained by the cyclohexane was separated and collected in the Dean-Stark trap until a total of 42.00 ml was removed. The time required for the reaction to this point was approximately 2 to 2.5 hours.

The reaction mass was allowed to cool. It was then filtered through a 0.5 inch bed of "Celite" diatomaceous earth supported by a 3 liter, coarse sintered glass filter.

Next, a 12 liter, 4-necked flask with a hemispherical bottom heating mantle, an air motor driven paddle stirrer, a steam source with condensate trap, a nitrogen purge, and an efficient take off condenser was charged with 700 ml deionized water and 2 gallons of the filtered reaction mass from above. The mixture was stirred briskly while 100.0 g of calcium hydroxide was added, and steam flow was introduced below the surface of the liquid charge. The steam distillation was continued until 8 l of water were collected. The contents of the 12 liter flask were allowed to cool to 80° C. before vacuum withdrawal to a vacuum filter flask.

The filter flask contents were filtered using a 25 cm plastic funnel with #1 filter paper. The filter was blanketed with nitrogen during filtration. The warm filtrate was transferred to a 4 liter separatory funnel. Approximately 1 hour was required for the aqueous caustic, yellow, bottom phase to separate. This was discarded. The upper organic phase containing the polyether formal glycol was purged with a steam of nitrogen at 120° C. for major water removal. One liter of toluene and 80 g calcium oxide were added and the mixture stirred over night. The slurry was next filtered through a bed of Celite diatomaceous earth, the toluene distilled off, 0.50 g of "Ionol" (butylated hydroxytoluene) antioxidant added and the polymer heated at 120° C./0.10 mm Hg for 12 hours for final drying.

The product characteristics of the TERATHANE ® poly(teramethylene ether formal) glycol were as follows:

$M_n$ (Infrared hydroxyl band method)=2393
$M_n$ (Hydroxyl No. method)=2272
Viscosity (40° C.)=9.04 poise
Color=<5.0 APHA
Crystalline melting point=19.83° C.

EXAMPLE 2

Preparation of Terathane ® 650/Peg 200 Poly(Ether Formal) Glycol

A 5 liter flask equipped as in EXAMPLE 1 was charged with the following:
1950 g TERATHANE ® 650
600 g Polyethyleneoxide Glycol 200, Mn 200
150.6 g Paraformaldehyde
1000 ml Cyclohexane
108.0 g Catalyst KO As little as 135.1 g and as much as 165.2 g of paraformaldehyde can be used in the above charge. This charge was heated at reflux under a nitrogen atmosphere, with mechanical stirring, and a Dean-Stark trap for collection and separation of water entrained with the cyclohexane. The cyclohexane was returned to the reaction vessel. The final molecular weight of the poly(ether glycol) formal may be modulated by taking off more or less water as desired. The time required to remove a given volume of water near the theoretical amount is inversely proportional to the amount of excess formaldehyde used.

The cooled reaction mass was filtered through a bed of diatomaceous earth filter aid, and the cyclohexane was removed from the crude formal filtrate by distillation.

The crude formal was transferred to a 12 liter flask and, after charging 750 ml water and 100 g calcium hydroxide, the mixture was steam purged for 2 hours. Next, the mixture was filtered through a bed of diatomaceous earth. The generally yellow aqueous phase of the filtrate was separated from the colorless polymer phase. The latter was purged with a stream of nitrogen at 120° C. for major water removal, 1 liter of toluene and 80 g calcium oxide were added, and the resulting mixture was stirred over night. On the next day the mixture was filtered through a bed of diatomaceous earth, toluene was distilled off, 0.50 g of "Ionol" butylated hydroxytoluene antioxidant was added, and the hybrid poly(ether formal) glycol was heated at 120° C./0.10 mm Hg for 12 hours for final drying.

The hybrid poly(ether formal) glycol characteristics were as follows:
Oxybutylene/oxyethylene ratio=1.00/0.410
Mn (Hydroxyl No. Method)=1654
Viscosity at 40° C.=4.42 poise
Crystalline melting point=22.51° C.
Color=40 APHA

EXAMPLE 3

Preparation of Terathane ® 650/Polypropylene Glycol 425 Poly(Ether Formal) Glycol A reaction vessel as in EXAMPLE 2 was charged with the following ingredients:
1300 g TERATHANE ® POLYETHER GLYCOL 650

425 g Polypropylene Glycol 425
90.3 g Paraformaldehyde
108.0 g Catalyst KO
1000 ml Cyclohexane As in EXAMPLE 2, the vessel was heated until 44.0 ml of water of reaction were removed in the Dean-Stark trap. The reaction mass was worked up in the usual manor, with calcium hydroxide, steam distillation, filtration, phase separation, drying over calcium oxide in cyclohexane, a second filtration, and final drying at 110° C./0.1 mm Hg.

Four charges as above were combined to give 5788 g of hybrid poly(ether formal) glycol having the following properties:

Oxytetramethylene/Oxypropylene ratio = 1.00/0.40
Mn (Hydroxyl No. method) = 1938
Mn (Infrared Hydroxyl band method) = 2226
Crystalline melting point = 14.34° C.
Viscosity at 40° C. = 7.21 poise
Color = 14 APHA Note the melting point is 4°-5° C. lower than the TERATHANE poly(ether glycol) starting material.

EXAMPLE 4

Preparation of Poly(Oxybutylene Formal) Glycol from 1,4 Butanediol and Formaldehyde A mixture of the following was charged to a reaction vessel as in previous examples:

1802 g 1,4-butanediol
1500 ml cyclohexane
108.7 g Catalyst KO
702.7 g paraformaldehyde The vessel was then heated to removed 360 ml water using the Dean-Stark trap. The reaction mass was filtered through diatomaceous earth filter aid, and the filtrate was concentrated using a rotorary evaporator to give 1600 g of crude formal. Continuous extraction of the crude formal with 4 gal of heptane followed by evaporation of the heptane from the heptane insoluble phase yielded 1239 g of the poly(oxybutylene formal) glycol.

The above procedure was repeated twice more with take off of 368 g water to give 1389 g (Mn by hydroxyl no. = 799) and 1410 g (Mn by hydroxyl number 8730). It was noted in determining the hydroxyl number of these two samples that the normally colorless acetylation mix became noticeably brown. Therefore, it was decided to remove color forming impurities by steam distillation from a basic solution containing calcium hydroxide.

A mixture of 2000 g of the two reaction products (1389 and 1410 g)
756 ml water
75 g Calcium oxide was charged to a steam distillation apparatus. The hot mixture remained colorless as the temperature rose to 98°-100° C. At 99° C. a deep, darkening, yellow color forming reaction set in along with precipitation of a yellow solid. The steam distillation was carried out for one hour. The remaining charge was cooled, the organic phase was separated, washed with water until neutral, and evaporated using toluene to remove adventious water. The residual polymer was added to 2 liters toluene and 200 g CaO, stirred overnight, and then filtered. The filtrate was evaporated and dried at 120° C. and 0.1 mm Hg pressure.

The final poly(oxybutylene formal) glycol was characterized as follows:

Mn (Hydroxyl No.) = 832
Viscosity (40° C.) = 1.60 poise
Color = <10 APHA
Crystalline melting point = 6.32° C.

The $^{13}$C—NMR spectrum of the above poly(oxybutylene formal) glycol exhibited a predominant peak at 95.06 ppm (relative to tetramethylsilane) consistent with the single formal unit in the repeating unit of $[O(CH_2)_4OCH_2]_m$ and a peak at 91.54 ppm consistent with the block polyformal unit $—O(CH_2O)_m—$ in the polyol chain. The reference spectrum of poly(oxyethylene/oxymethylene) formal shows a $^{13}$C—NMR resonance at 91 ppm for $—O(CH_2O)_m—$ (Quano-Tho-Pham et al., "Proton and Carbon NMR Spectra of Polymers", Vol. 2, p. 332, John Wiley and Sons, 1983). Therefore, the poly(oxybutylene oxymethylene) glycol of this invention has 16% of all the oxymethylene units as block $—(OCH_2)_m—$ units by NMR analysis. This is a surprising finding and the block oxymethylene units must surely give additional interruptions to the order of alignment of adjacent poly(oxybutylene formal) glycol chains or their derived end-use polymers.

A 1250 g sample of this poly(oxybutylene formal) glycol was used in preparing polyurethane compositions as reported in EXAMPLE 6.

The formals were prepared from mixtures of the glycols defined above with paraformaldehyde or other formaldehyde equivalent species in the molar ratio of n moles of glycol to 0.9 to 1.5 (n−1) moles of formaldehyde equivalent. In the example of TERATHANE ® 650/PEG 200 co-formal glycol (EXAMPLE 2), the amount used was 1.0 (n−1) moles formaldehyde equivalent per mole of glycol. The use of greater amounts of formaldehyde [<1.0 (n−1)] afforded a more rapid generation of water to the end point, yet gave greater amounts of impurities (related to the excess of formaldehyde used) to be removed in the calcium hydroxide purification treatment.

For the azeotropic removal of water formed during the formal condensation, any one of a variety of hydrocarbon solvents may be used, although the preferred solvent is cyclohexane with a boiling point of 80.7°–81.0° C. Removal of water at this temperature is close to maximizing the rate of water formation while at the same time limiting the depolymerization of the poly(tetramethylene ether) glycol to monomers in the presence of acidic catalysts. Avoiding depolymerization of the PTMEG affords superior poly(ether formal) glycol yields and superior molecular weight control of the final polymer.

The amount of hydrocarbon solvent used to remove water is not critical to the success of the reaction, although an amount approximately equal the weight of the poly(ether) glycol used in the reaction is efficacious.

EXAMPLE 5

Conversion of Terathane ® 650×3 Formal Glycol [Poly(Tetramethylene Ether Formal) Glycol] to a Polyurethane A poly(tetramethylene formal) glycol was prepared by coupling three moles of TERATHANE ® 650 with approximately 2 moles of paraformaldehyde following the procedure described in EXAMPLE 1. The number average molecular weight of the product poly(tetramethylene ether formal) glycol was 2017.

A 2 liter flask fitted with an external heater, an internal thermometer, and a stirrer was continually purged with dry nitrogen and used as a reaction vessel to convert the poly(ether formal) glycol first to a polyol prepolymer and finally to a polyurethane. The reaction vessel was charged with 1 mole (174 g) of toluene diisocyanate (TDI Mondur ® TDS) and 0.5 moles (1009 g) of the above poly(ether formal) glycol. After the initial exotherm subsided, the reaction mass was held at 80° C. for 2 hours, and then allowed to cool overnight.

On the next day the percent isocyanate content of the polyol prepolymer was determined to be 3.40% as —NCO by titration of an aliquot with dibutylamine versus 3.55% calculated theoretical value. The viscosity of the prepolymer was 820 cP at 80° C. and 7080 cP at 30° C. This is in contrast to a similar prepolymer of poly(tetramethylene ether) glycol of 2000 number average molecular weight with a viscosity of 1890 cP at 80° C. and 16,340 cP at 30° C.

The previously prepared prepolymer of the poly(tetramethylene ether formal) glycol was chain extended with methylene-bis(o-chloroaniline) [MBCA] as follows:

A 250 g sample of prepolymer was heated at 90° C. and 10.3 g MBCA (95% stoichiometry) was added and quickly mixed with the prepolymer. The mixture was poured into molds heated to 120° C. and cured for 1 hour at 120° C. The molds were then cooled and the molded polyurethane parts were removed. The parts were then heat aged overnight at 100° C.

The polyurethane parts were subjected to physical tests and are compared with similar polyurethane parts made from poly(tertramethylene) glycol of 2000 number average molecular weight (Mn) in the following table:

EXAMPLE 6

Conversion of Poly(Oxybutylene Formal) Glycol to Polyurethanes

Representative samples of the poly(oxybutylene formal) glycol reaction product of 1,4-butanediol and para-formaldehyde prepared by the process described in EXAMPLE 4, except for a number average molecular weight of 832 and a viscosity at 40° C. of 1.60 poise, were prepared and converted to polyol prepolymers as in EXAMPLE 5. Toluene diisocyanate (TDI, Mondur ® TDS) was used with one sample of the poly(oxybutylene formal) glycol and methylene diphenylene-4,4'-diisocyanate (MDI) with a second sample. Composition and properties of the prepolymers are reported below:

| PREPOLYMER COMPOSITION | |
|---|---|
| TDI 2.0 moles | MDI 2.4 moles |
| POLY(OXYBUTYLENE FORMAL) GLYCOL | POLY(OXYBUTYLENE FORMAL) GLYCOL |
| —NCO % Content | —NCO % Content |
| Theory 7.12 | Theory 8.21 |
| Actual 7.60 | Theory 8.48 |

| PREPOLYMER PROPERTIES | | | |
|---|---|---|---|
| BROOKFIELD VISCOSITY TEMPERATURE VISCOSITY | | BROOKFIELD VISCOSITY TEMPERATURE VISCOSITY | |
| °C. | CPS. | °C. | CPS. |
| 80 | 210 | 80 | 346 |
| 30 | 3050 | 30 | 7000 |
| Clear and fluid after overnight storage at 39° F. | | Cloudy and fluid after overnight storage at 39° F. | |

| PHYSICAL TEST DATA | | |
|---|---|---|
| | POLYURETHANE FROM POLY(TETRAMETHYLENE ETHER FORMAL) GLYCOL Mn 2017 | POLYURETHANE FROM POLY(TETRAMETHYLENE ETHER) GLYCOL Mn 2000 |
| Hardness, A Scale | 78 | 80 |
| D Scale | 29 | |
| 100% Modulus, psi | 561 | 591 |
| 300% Modulus, psi | 867 | 1156 |
| Tensile Strength at break, psi | 4123 | 3826 |
| Elongation, % | 680 | 502 |
| Tear Strength | | |
| Trouser tear, pli | 53 | 43 |
| Graves tear, pli | 321 | 313 |
| Bayshore Rebound, % | 56 | 54 |
| Compression Set B Scale, % | 31 | 50 |
| Clashberg, $T_f$, °C.* | <−70 | <−70 |
| Torsional modulus. | | |
| psi at −60° C. | 7,187 | 20,500 |
| psi at −70° C. | 26,297 | 38,376 |
| Brittle point | | |
| Temperature, °C. | −100 | |
| Failures | 0 | |
| Temperature, °C. | −105 | |
| Water Vapor Transmission P g/100 Sq. in/24 hrs. | 5.161 | 4.970 |
| % Volume Increase in 1 week at 70 C. in: | | |
| #1 Oil | 3.39 | |
| #3 Oil | 26.36 | 30.10 |

*Clashberg, $T_f$ Temperature at which torsional modulus = 45,000 psi

The above TDI prepolymer was chain extended on the next day using MBCA (methylene bis(orthochloroaniline)) at 95% stoichiometry and a reaction temperature of 80° C. Likewise, the MDI prepolymer was chain extended on the next day with monomeric 1,4-butanediol (1,4-BDO) at 102% of stoichiometry and a reaction temperature of 85° C. Both compositions were quickly poured into molds heated to 120° C. and cured for 1 hour at 120° C. The polyurethane parts were then heat aged overnight at 100° C. Physical test data for the final aged samples are reported in the following table:

| PHYSICAL TEST DATA | | |
|---|---|---|
| POLYURETHANE FROM POLY (OXYBUTYLENE FORMAL) GLYCOL (Mn 832) with: | | |
| | TDI & MBCA | MDI & 1,4-BDO |
| Hardness, A Scale | 95 | 90 |
| D Scale | 55 | 42 |
| Stress/Strain-20 in/min-RT | | |
| 100% Elongation, psi | 2362 | 1289 |
| 300% Elongation, psi | 4351 | 1821 |
| Elongation at Break, % | 330 | 545 |
| psi | 4831 | 2430 |
| Tear Strength | | |
| Trouser tear, pli | 98 | 95 |
| Graves tear, pli | 444 | 333 |
| Bayshore Rebound, % | 36 | 42 |
| Compression Set B 22 hours @ 70° C. | 35 | 49 |
| Clashberg Temp. °C./psi | −30/30,680 −40/51,212 | −40/25,498 −50/49,256 |
| % Volume Increase 1 week at 70° C. in: | | |
| #1 Oil | −1.33 | −1.08 |
| #3 Oil | +3.99 | +3.98 |

I claim:

1. A process for the preparation of oligomeric formal diols comprising mixing and refluxing at 80°–81° C. cyclohexane solvent, formaldehyde, and one of the following glycols or mixtures of glycols, at a mole ratio in the range between 0.95(n−1) and 1.10(n−1) moles of formaldehyde per n mole of glycol in the presence of 1 to 10 weight percent (based on the weight of glycol) of solid montmorillonite catalyst:
   (a) poly(tetramethylene ether) glycol having a number average molecular weight of 650 to 3,000.
   (b) a mixture of poly(tetramethylene ether) glycol having a number average molecular weight of 650 to 3,000 and one or more glycols of the formula HO($C_xH_{2x}O$)$_n$H wherein x is 2 or 3 and n is from 5 to 50, or
   (c) a glycol of the formula HOC$_y$H$_{2y}$OH wherein y is 2 to 6;
removing a distillate consisting of water and cyclohexane from the formal reaction product of (a), (b), or (c) and recovering a formal reaction product of (a), (b), or (c) having a number average molecular weight of 500 to 10,000.

2. The process of claim 1 wherein the formaldehyde is mixed with (a) poly(tetramethylene ether)glycol having a number average molecular weight of 650 to 3,000.

3. The process of claim 2 wherein (a) has a number average molecular weight of about 650.

4. The process of claim 3 wherein the product of formaldehyde and (a) is purified by distillation with steam in the presence of 1.32 to 6.60 weight percent calcium hydroxide or 1 to 5 weight percent calcium oxide, based on product of formaldehyde and (a).

5. The process of claim 1 wherein the formaldehyde is mixed with (b) poly(tetramethylene ether) glycol having a number average molecular weight of 650 to 3,000 and one or more of a glycol of the formula HO($C_xH_{2x}O$)$_n$H where x is 2 or 3 and n is from 5 to 50.

6. The process of claim 5 wherein x is 2.

7. The process of claim 6 wherein number average molecular weight of said (polytetramethylene ether) glycol of (b) is about 650.

8. The process of claim 7 wherein the product of formaldehyde and mixture of glycols (b) is purified by distillation with steam in the presence of 1.32 to 6.60 weight percent calcium hydroxide, or 1 to 5 weight percent calcium oxide based on product of formaldehyde and mixture of glycols (b).

9. The process of claim 5 wherein HO($C_xH_{2x}O$)$_n$H is

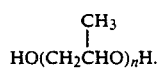

10. The process of claim 9 wherein the product of formaldehyde and mixture of glycols (b) is purified by distillation with steam in the presence of 1.32 to 6.60 weight percent calcium hydroxide, or 1 to 5 weight percent calcium oxide based on product of formaldehyde and mixture of glycols (b).

11. The process of claim 1 wherein the formaldehyde is mixed with (c) a glycol of the formula HOC$_y$H$_{2y}$OH where y is 2 to 6.

12. The process of claim 11 wherein said glycol is 1,4-butanediol.

13. The process of claim 11 wherein the product of formaldehyde and diol (c) is purified by distillation with steam in the presence of 1.32 to 6.60 weight percent calcium hydroxide, or 1 to 5 weight percent calcium oxide based on product of formaldehyde and (c).

* * * * *